US005656761A

United States Patent [19]

Nagahara et al.

[11] Patent Number: 5,656,761
[45] Date of Patent: Aug. 12, 1997

[54] METHOD FOR PRETREATING A CATALYST SLURRY AND A METHOD FOR THE CONTINUOUS PARTIAL HYDROGENATION OF A MONOCYCLIC AROMATIC HYDROCARBON BY USING THE PRETREATED CATALYST SLURRY

[75] Inventors: Hajime Nagahara; Koji Nakagawa, both of Kurashiki, Japan

[73] Assignee: Asahi Kasei Kogyo Kabushiki Kaisha, Osaka, Japan

[21] Appl. No.: 243,398

[22] Filed: May 16, 1994

Related U.S. Application Data

[63] Continuation of Ser. No. 781,163, filed as PCT/JP91/01076, Aug. 13, 1991, abandoned.

[51] Int. Cl.$^6$ .................. C07C 5/11; B01J 23/46
[52] U.S. Cl. .................. 585/269; 585/206; 585/271; 585/273; 585/277; 502/325; 502/326; 502/328; 502/329
[58] Field of Search .................. 585/266, 269, 585/271, 273, 277; 502/325, 326, 328, 329

[56] References Cited

U.S. PATENT DOCUMENTS

| | | | |
|---|---|---|---|
| 4,055,512 | 10/1977 | Kageyama et al. | 502/74 |
| 4,665,274 | 5/1987 | Ichiharhi et al. | 585/267 |
| 4,678,861 | 7/1987 | Mitsui et al. | 585/266 |
| 4,734,536 | 3/1988 | Nagahara et al. | 585/269 |

FOREIGN PATENT DOCUMENTS

| | | |
|---|---|---|
| 0323192 | 5/1989 | European Pat. Off. . |
| 60-255738 | 12/1985 | Japan . |
| 62-67033 | 3/1987 | Japan . |
| 62-81332 | 4/1987 | Japan . |
| 129174 | 6/1989 | Japan . |

OTHER PUBLICATIONS

Abstract of JP-A-32 38 047

*Primary Examiner*—Ponnathapura Achutamurthy
*Attorney, Agent, or Firm*—Birch, Stewart, Kolasch & Birch, LLP

[57] ABSTRACT

A method for pretreating a slurry containing a ruthenium catalyst for use in the continuous partial hydrogenation of monocyclic aromatic hydrocarbons is disclosed. In this method, the above-mentioned slurry is heat-treated at a temperature of from 60° to 180° C. for at least 10 minutes while agitating. By using the pretreated catalyst slurry in the above-mentioned continuous partial hydrogenation, partial hydrogenation reaction products can be efficiently obtained without suffering from the excess mixing of the components of the catalyst slurry into an oil phase containing the partial hydrogenation reaction products, thereby enabling operations and facilities required for separation to be simplified.

17 Claims, No Drawings

METHOD FOR PRETREATING A CATALYST SLURRY AND A METHOD FOR THE CONTINUOUS PARTIAL HYDROGENATION OF A MONOCYCLIC AROMATIC HYDROCARBON BY USING THE PRETREATED CATALYST SLURRY

This application is a continuation of application Ser. No. 07/781,163, filed as PCT/JP91/01076, Aug. 13, 1991, now abandoned.

TECHNICAL FIELD

The present invention relates to a method for pretreating a catalyst slurry and a method for the continuous partial hydrogenation of monocyclic aromatic hydrocarbons using the pretreated catalyst slurry. More particularly, the present invention is concerned with a method for pretreating a catalyst slurry in which a slurry containing a ruthenium catalyst is heat-treated, and a method in which the partial hydrogenation of monocyclic aromatic hydrocarbons is carried out using the pretreated catalyst slurry to thereby efficiently, stably and continuously produce and recover corresponding cycloolefins, especially cyclohexenes.

Cyclohexenes are highly valuable in the commerce as intermediates for the manufacture of organic chemical engineering products, and particularly, they are important as intermediates for the production of polyamides and lysines.

BACKGROUND ART

Various methods have been proposed for producing cyclohexenes using as starting materials monocyclic aromatic hydrocarbons. For example, it has been proposed to use (1) a method using water, an alkali agent and a catalyst composition containing a member selected from the Group VIII elements of the Periodic Table [Japanese Patent Publication (Kokoku) No. 56-22850/1981]. Further, it has been proposed to use (2) a method in which a reaction is carried out in the presence of a ruthenium catalyst and a neutral or an acidic aqueous solution containing a salt of a cation of at least one member selected from the group consisting of Group IA and Group IIA metals of the Periodic Table and manganese [Japanese Patent Publication (Kokoku) No. 57-7607/1982]. Still further, it has been proposed to use (3) a method in which a reaction is carried out in the presence of a ruthenium catalyst dispersed in silica gel derived from a hydrolysis product of a silicon alkoxide, and water [Japanese Patent Publication (Kokoku) No. 60-59215/1985]. Still further, it has been proposed to use (4) a method in which a reaction is carried out in the presence of a catalyst comprising ruthenium supported on barium sulfate, water and an additive [Japanese Laid-Open Patent Application (Kokai) No. 61-40226/1986]. Still further, it has been proposed to use (5) a method in which a reaction is carried out in the presence of a catalyst comprising ruthenium supported on a compound containing a rare earth element, water and an alkali agent [Japanese Patent Publication (Kokoku) No. 1-29174/1989]. Still further, it has been proposed to use (6) a method in which a reaction is carried out in the presence of metallic ruthenium particulates, zirconium oxide or hafnium oxide, and water [Japanese Laid-Open Patent Application (Kokai) No. 62-81332/1987]. Still further, it has been proposed to use (7) a method in which a reaction is carried out in the presence of a ruthenium catalyst using as a starting material a monocyclic aromatic hydrocarbon which substantially does not contain a sulfur compound [Japanese Laid-Open Patent Application (Kokai) No. 60-255738/1985]. Still further, it has been proposed to use (8) a method in which a reaction is carried out in the presence of a ruthenium catalyst and water in an atmosphere which does not cause iron to be deposited on the catalyst [Japanese Laid-Open Patent Application (Kokai) No. 62-67033/1987]. In all of these methods, catalyst slurries prepared by dispersing or dissolving a ruthenium catalyst and various types of additives in water are brought into contact with monocyclic aromatic hydrocarbons and hydrogen by mixing in a liquid phase, thereby obtaining cycloolefins.

When a practical process for continuously producing cycloolefins is designed according to these conventional methods, it is requisite to effect complete separation between a catalyst slurry comprised of a ruthenium catalyst and water (hereinbelow frequently referred to simply as "aqueous phase") and an oil phase containing a partial hydrogenation reaction product and an unreacted monocyclic aromatic hydrocarbon (hereinbelow frequently referred to simply as "oil phase"). With such a process, if components of the aqueous phase, for example, excess amounts of a catalyst and/or an additive (such as a solid material, an alkaline material, or an acidic material which is added for improvement and stabilization of reaction performance.) get mixed into the oil phase, problems, such as clogging of process pipes or corrosion of conventionally used apparatus materials, would occur due to the mixed components. Such problems can be solved to a certain extent by providing, for example, a filtering device or a washing device for removing the mixed components. However, in the commercial practice, facilities and operations therefor are inevitably accompanied with difficulties. Further, in a continuous partial hydrogenation reaction as well, it is apparent that when excess amounts of a catalyst and/or an additive get mixed, and even when gradually get mixed into the oil phase, and flow away, some measures and facilities must be provided for keeping the reaction system stable for a prolonged period of time.

Accordingly, from a commercial viewpoint, means for preventing components of the aqueous phase from excessively getting mixed into the oil phase is strongly desired.

The term, "excess" used herein means an amount in excess of the solubility of components of the aqueous phase in an oil phase under partial hydrogenation reaction conditions or phase separation conditions (for example, the temperatures employed, and the composition of the oil phase generally comprising a reaction product and an unreacted starting material). As a practical matter, however, problems arise when excess amounts of several times the solubility get mixed. Therefore, more specifically, the term "excess" used herein means several or more times the solubility. For example, according to the study of the present inventors, when a partial hydrogenation reaction of benzene is conducted at a hydrogen pressure of 50 kg/cm$^2$G and at 150° C. using as an aqueous phase a catalyst and an 18 % by weight aqueous $ZnSO_4.7H_2O$ solution (which is an additive to be added for improvement and stabilization of a reaction yield) to thereby obtain a reaction mixture comprised of 50 mole % of benzene and 50 mole % of a mixture of cyclohexene and cyclohexane, the solubility of water in the oil phase is about 1% by weight, and the solubility of $ZnSO_4$ in the oil phase is 1 ppm or less (the solubility thereof in water dissolved in the oil phase is 100 ppm or less). In this instance, the meaning of "excess" is several times, for example, two or three times the above-mentioned solubility of about 1% by weight with respect to water and 1 ppm with respect to $ZnSO_4$. In addition, it is noted when the above-mentioned excess mixing of water and $ZnSO_4$ occurs, the mixing of solid, components of the aqueous phase into the oil phase is also observed in most cases.

From this viewpoint, a review is made of the conventional technologies. For example, with respect to the above-described prior art methods (1) to (6), although there is a description regarding a continuous reaction according to a liquid phase suspension method, only a batch reaction is conducted in the Examples thereof and there is no description regarding an attempt to almost completely separate a catalyst slurry from an oil phase, which separation is aimed at by the present invention.

Further, the above-described prior art methods (5) to (8) are the methods developed by the present inventors themselves. Especially in the methods (7) and (8), the partial hydrogenation reaction of monocyclic aromatic hydrocarbons is continuously carried out using a catalyst slurry comprised of a ruthenium catalyst and water. In the prior art methods (7) and (8), continuous reaction was actually performed, and partial hydrogenation reaction was successfully performed over a period of 100 to 500 hours at relatively stable reaction performance. However, there is no description regarding materials having gotten mixed into the collected oil phase and the amounts thereof, and no study has been conducted with respect to almost complete separation of the catalyst slurry from the oil phase, which separation is aimed at by the present invention.

DISCLOSURE OF INVENTION

The present inventors have carried out continuous partial hydrogenation reactions using various types of catalyst slurries with respect to monocyclic aromatic hydrocarbons which were continuously flowed and fed to a reaction zone, and have made detailed investigations not only on reaction performance but also on the separation between an aqueous phase and an oil phase. As a result, the present inventors have found that when such a reaction comprising a flow step (flow reaction) is easily started, a portion of the components of the catalyst slurry which should be essentially retained in the aqueous phase gets mixed into the oil phase and flowed away, thereby causing adverse effects on the subsequent process operations and materials. Further, the present inventors have determined that this phenomenon rather generally occurs although the occurrence of this phenomenon depends on the difference of the components of the catalyst slurry. Still further, it has been found that this phenomenon cannot be recognized by only observing a reaction mixture after conducting an ordinary batch reaction, and that in some cases, this phenomenon is observed in a continuous reaction although the oil phase appears to be clearly separated from the aqueous phase after the batch reaction. Still further, the present inventors have found that in order to prevent the phenomenon, it is not sufficient to only provide a stationary separating vessel having a sufficient size for separating most of the catalyst slurry from the oil phase.

The present inventors have extensively and intensively studied with a view toward avoiding such a phenomenon, to thereby complete the present invention. According to one aspect of the present invention, there is provided a method for pretreating a catalyst slurry for use in the continuous partial hydrogenation of monocyclic aromatic hydrocarbons by the reaction with a hydrogen gas, which comprises heat-treating a catalyst slurry comprised mainly of a ruthenium catalyst and water, while agitating, at a temperature of from 60° to 180° C. for at least 10 minutes, prior to the use of the catalyst slurry in the continuous partial hydrogenation of the aromatic hydrocarbon.

In another aspect of the present invention, there is provided a method for the continuous partial hydrogenation of monocyclic aromatic hydrocarbons, which comprises: (1) continuously feeding a monocyclic aromatic hydrocarbon and a hydrogen gas to a reaction zone to effect a contact thereof with a catalyst slurry comprised mainly of a ruthenium catalyst and water and perform a partial hydrogenation reaction of the aromatic hydrocarbon, the catalyst slurry having been heat-treated at a temperature of from 60° to 180° C. for at least 10 minutes while agitating, thereby obtaining a reaction mixture comprising an oil phase comprised mainly of a partial hydrogenation reaction product and the unreacted aromatic hydrocarbon and an aqueous phase comprised of the catalyst slurry; and (2) continuously introducing the reaction mixture to an oil phase-aqueous phase separation zone to separate the oil phase from the aqueous phase.

When the pretreatment of the present invention is carried out under suitable conditions, the desired activity and selectivity of the catalyst with respect to the partial hydrogenation reaction of monocyclic aromatic hydrocarbons can be stably obtained as from immediately after the start of the flow reaction. Further, an improvement of the selectivity itself is sometimes attained.

Hereinbelow, the particular embodiments of the present invention will be described. The catalyst slurry comprised of a ruthenium catalyst and water to be used in the present invention comprises as essential components a ruthenium catalyst and water. In addition, the catalyst slurry may further comprise various types of additives, as described hereinbelow.

Examples of ruthenium catalysts include metallic ruthenium particulates and ruthenium supported on various carriers, for example, rare earth element compounds, oxides and hydroxides of Ti, Zr, Hf, Nb, Ta, Cr, Fe, Co, Al, Ga and Si, hydrates of such oxides and hydroxides, and water insoluble salts, such as barium sulfate. The ruthenium catalyst may contain catalyst components other than ruthenium, such as Cu, Fe, Zn and Ag. To improve reaction performance and effect reaction stabilization, the following additives can be added to the ruthenium catalyst. The additives include a variety of soluble and insoluble materials, such as salts of a Group IA metal, a group IIA metal, Zn and Co, various alkali agents (reagents for alkalinization, such as NaOH and ammonia), oxides and hydroxides of Ti, Zr, Hf, Nb Ta, Cr, Fe, Co, Al, Ga and Si, hydrates of such oxides and hydroxides, and activated carbon.

Especially, a method in which metallic ruthenium particulates and, as a solid additive, an oxide or a hydroxide of Ti, Zr, Hf, Nb, Ta, Cr, Fe, Co, Al, Ga, Si or a hydrate thereof are used with an aqueous solution of a Zn salt (for example, the above-mentioned prior art method (6)) can be preferably employed because the selectivity and yield are high in the preparation of cycloolefins by partial hydrogenation reaction.

The amount of catalyst to be used depends on the form of the catalyst. When metallic ruthenium particulates are used, the catalyst is used in an amount of from $1\times10^{-5}$ to 0.1 part by weight, preferably from $1\times10^{-4}$ to $5\times10^{-2}$ part by weight, per part by weight of coexisting water. When a catalyst comprised of ruthenium supported on a carrier is used, the catalyst is used in an amount of from $1\times10^{-4}$ to 0.3 part by weight, preferably from $1\times10^{-3}$ to 0.1 part by weight, per part by weight of coexisting water. Further, when a solid additive is used in addition to the catalyst itself, the total amount of the catalyst and the solid additive other than the catalyst, that is, the slurry concentration, is in the range of from $1 \times 10^{-3}$ to 0.3 part by weight, preferably from $1 \times 10^{-2}$ to 0.1 part by weight, per part by weight of coexisting water. When the additive is soluble in water, the amount thereof can be chosen in the range of from several parts per million to solubility.

Examples of monocyclic aromatic hydrocarbons to be fed to a partial hydrogenation reaction zone include benzene, toluene, xylenes, and lower alkylbenzenes with an alkyl group having 2 to 4 carbon atoms. The partial hydrogenation reaction is generally conducted at a temperature of from 100° to 200° C. under a hydrogen pressure of from 10 to 100 kg/cm²G. The time for contact of the monocyclic aromatic hydrocarbon with the catalyst is generally in the range of from about 1 minute to 10 hours. The reaction mixture to be withdrawn as an oil phase is a mixture of a cyclohexene, a cyclohexane and an unreacted starting material. The method for separating the desired reaction product from the unreacted material is not limited, and any one of the conventional methods can be employed. For example, separation can be performed by distillation.

The pretreatment of a catalyst slurry according to the method of the present invention is conducted in a condition such that oil phase components, such as a monocyclic aromatic hydrocarbon as a starting material, are not present. However, a small amount of oil phase components can be present as long as it is soluble in the aqueous phase under pretreatment conditions. Further, the pretreatment of the present invention is carried out for the catalyst slurry which is for the first time to be used for a partial hydrogenation reaction. The pretreatment according to the present invention is not necessarily required for the catalyst slurry which has once been pretreated and which has already been used in the partial hydrogenation reaction and then cooled for reuse in a partial hydrogenation reaction.

The gaseous phase under which the pretreatment of the present invention is performed may be comprised of steam, hydrogen, air or nitrogen. The type of the gas is not especially limited as long as it does not have an adverse effect on the catalyst. Generally, however, a hydrogen or a nitrogen atmosphere is preferred. Moreover, when the pretreatment is conducted in the presence of hydrogen, that is, in the presence of hydrogen dissolved in the catalyst slurry, the desired activity and selectivity of the catalyst for the partial hydrogenation reaction of monocyclic aromatic hydrocarbons can be stably ensured as from immediately after the start of flow reaction, and in some cases an improvement of the selectivity itself is attained. Therefore, the above-mentioned method for the pretreatment is advantageous. In such a method, the pretreatment is conducted at a hydrogen pressure of from 1 to 100 kg/cm²G, preferably under the same pressure as that in the partial hydrogenation reaction.

The pretreating method of the present invention is conducted at a temperature of from 60° to 180° C. When the temperature is lower than 60° C., an extremely prolonged period of time is undesirably required for the pretreatment, or the effects aimed at by the present invention cannot be obtained. On the other hand, when the temperature is higher than 180° C., denaturization of the catalyst itself sometimes occurs to disadvantages. It is preferred that the pretreatment be conducted at a temperature of from 100° to 150° C.

In the present invention, it is requisite to conduct the pretreatment for a period of at least 10 minutes under the above-described conditions. A preferred treating period varies depending on the types of components of the catalyst slurry and the treatment temperature. Generally, however, the treating period is at least 10 minutes, generally in the range of from several hours to several days.

The reason why in a continuous partial hydrogenation reaction, a complete separation is attained between an aqueous phase (a catalyst aqueous phase) and an oil phase by the pretreatment of the catalyst slurry according to the present invention, so that the components of the catalyst slurry are inhibited from getting mixed into the oil phase, has not yet been elucidated: However, it is presumed as follows: Even in a compound generally known as a hydrophilic compound, a lipophilic surface is partially formed thereon as viewed micro-scopically, which lipophilic surface is likely to cause the compound to get mixed into the oil phase. However, this lipophilic surface would be changed to a hydrophilic surface by the pretreatment of the present invention.

By virtue of the present invention, a desired partial hydrogenation reaction product can be continuously obtained without suffering from the excess mixing of the components of the catalyst slurry into the oil phase and, hence, the operations, facilities and the like which are required for separation can be streamlined on an industrial scale. The method of the present invention is highly valuable in the commerce.

BEST MODE FOR CARRYING OUT THE INVENTION

The present invention will now be further illustrated in more detail with reference to the following Examples which should not be construed to be limiting the scope of the present invention.

The preparation methods of the catalyst slurries employed in Examples 1, 2 and 4 hereinbelow are the same as those described in the Examples of U.S. Pat. No. 4,734,536, and the preparation method of the catalyst slurry employed in Example 3 hereinbelow is the same as that described in the Example of U.S. Pat. No. 4,678,861.

EXAMPLE 1

A catalyst slurry comprised of 2.5 g of a metallic ruthenium particulate catalyst (average crystallite size, 55 Å) containing 7.4 % by weight of zinc, which ruthenium catalyst had been obtained by reducing $Ru(OH)_3$ having contained zinc hydroxide, 15 g of $ZrO_2$ powder (average particle size, 0.35 µ), and 1,400 ml of an 18 % aqueous solution of $ZnSO_4.7H_2O$ containing 250 mg of $ZnSO_4.3Zn(OH)_2$, was charged into a continuous flow reaction apparatus having an inner capacity of 3 liters which was provided therein with an about 100 ml stationary vessel for oil phase-aqueous phase separation (equipped with an inlet for a reaction mixture, an outlet for an aqueous phase, and an outlet for an oil phase) and had Teflon coating applied at portions to be brought into contact with the liquid.

Next, the gaseous phase was replaced by a hydrogen gas, and the temperature was elevated to 150° C. over a period of one hour while agitating the catalyst slurry. Subsequently, hydrogen was introduced to attain a total internal pressure of 50 kg/cm²G, which was kept for 20 hours. Thus, pretreatment of the catalyst slurry was performed. Thereafter, benzene was fed at a rate of 2 liter/hr, and the partial hydrogenation reaction of benzene was continuously carried out while maintaining a temperature of 150° C. and a hydrogen pressure of 50 kg/cm²G.

The aqueous phase discharged from the stationary vessel for oil phase-aqueous phase separation was recycled to the reaction system, while the oil phase discharged was cooled and passed through a polypropylene microporous filter. The water contents precipitated from the oil phase due to the occurrence of a supersaturated state caused by the cooling and the components of the catalyst slurry excessively mixed into the oil phase, were aggregated and filtered to thereby separate the same from the oil phase. Thus, the oil phase as a reaction product was continuously withdrawn. On the other hand, the separated and collected water and water-soluble components were appropriately recycled to the reaction apparatus. These operations were continuously carried on for 500 hours, thereby obtaining a partial hydrogenation reaction mixture comprised of benzene, cyclohexene and cyclohexane.

An aliquot of the separated and collected water was taken out, and the amount of the water-soluble component ($ZnSO_4$ and the like) of the catalyst slurry contained in the collected water was analyzed to find that the content of this component was as small as 10–30 ppm in terms of the amount of Zn by weight relative to the weight of the separated and collected water. After the completion of flow reaction, the microporous filter was taken out, and the deposition of solid materials thereon was examined. The amount of white $ZrO_2$ deposited was only of a trace. From the above, it is apparent that the amount of components of the catalyst slurry which got mixed into the oil phase during the flow reaction was extremely small, so that substantially no material got mixed into the oil phase, except only the water, the amount of which corresponded to the solubility of water in the oil phase at 150° C.

EXAMPLE 2

Substantially the same procedure as in Example 1 was repeated to perform a continuous reaction for 200 hours, except that the pretreatment operation of the catalyst slurry was conducted by elevating the temperature to 80° C. over a period of 30 minutes, and the pretreatment was continued for 48 hours at the same temperature. The content of Zn in the water separated and collected during the continuous reaction was 10–50 ppm by weight. Further, the amount of white $ZrO_2$ deposited on the microporous filter was of a trace, and the amount of components of the catalyst getting mixed into the oil phase during the flow reaction was extremely small. From the above, it is apparent that substantially no material got mixed into the oil phase, except the water, the amount of which corresponded to the solubility of water in the oil phase at 150° C.

Comparative Example 1

Substantially the same procedure as in Example 1 was repeated to perform a continuous reaction for 200 hours, except that the pretreatment of the catalyst slurry was not carried out, and that in the process of temperature elevation to 150° C., feeding of benzene was started at the time when the temperature reached 100° C. by heating for five minutes. The content of Zn in the water separated and collected during the continuous reaction was 80–600 ppm by weight. About 1.0 g of a mixture of white $ZrO_2$ and the ruthenium catalyst was deposited on the microporous filter. From the above, it is apparent that the components of the catalyst slurry excessively got mixed into the oil phase.

EXAMPLE 3

Pretreatment of a catalyst slurry and a partial hydrogenation reaction of benzene were carried out in substantially the same manner as in Example 1, except that a catalyst slurry comprised of 70 g of a hydrogenating catalyst composed of 1% of ruthenium supported on lanthanum hydroxide, 700 mg of zinc oxide, 35 g of sodium hydroxide and 1400 ml of water used. During the reaction, an aliquot of the separated and collected water was taken out, and the amount of components of the catalyst slurry which was contained therein was analyzed. The amount of Na was as small as 30 to 70 ppm by weight, and the amount of Zn was less than 0.2 ppm by weight, relative to the weight of the separated and collected water. After the completion of the flow reaction, the microporous filter was taken out and examined to determine solid components deposited thereon. Only a trace amount of hydrogenating catalyst was observed.

Comparative Example 2

Substantially the same procedure as in Comparative Example 1 was repeated to perform a continuous reaction, except that the same catalyst slurry as used in Example 3 was used. The amount of Na contained in the water separated and collected during the continuous reaction was 150–500 ppm by weight, and the amount of Zn contained therein was 0.5–2 ppm by weight. After the completion of the flow reaction, deposition of about 2.5 g of the hydrogenating catalyst was observed on the microporous filter.

EXAMPLE 4

Substantially the same procedure as in Example 1 was repeated to perform a continuous reaction, except that the gaseous phase was replaced by nitrogen at atmospheric pressure in the pretreatment of the catalyst slurry. The amount of Zn contained in the water separated and collected during the continuous reaction was 10–60 ppm. Only a trace amount of white $ZrO_2$ was deposited on the microporous filter. From the above, it is apparent that the amount of components of the catalyst slurry which got mixed into the oil phase during the flow reaction was extremely small. The selectivity for cyclohoxene immediately after the start of the flow reaction was about 3% lower than that obtained in Example 1.

Industrial Applicability

By virtue of the present invention, the continuous partial hydrogenation of monocyclic aromatic hydrocarbons can be efficiently attained. In the present invention, partial hydrogenation reaction products can be efficiently obtained without suffering from the excess mixing of the components of the catalyst slurry into an oil phase containing the partial hydrogenation reaction products, and operations and facilities required for separation can be simplified. The partial hydrogenation products of monocyclic aromatic hydrocarbons efficiently obtained by the present invention are highly valuable as intermediates for the manufacture of organochemical industrial products, and particularly, they are important as intermediates for the production of polyamides and lysines.

We claim:

1. A method for pretreating a catalyst slurry for use in the continuous partial hydrogenation of a monocyclic aromatic hydrocarbon by the reaction with a hydrogen gas, which comprises heat-treating a catalyst slurry comprised mainly of a ruthenium catalyst, a Zn salt and water substantially in the absence of said monocyclic aromatic hydrocarbon, while agitating, at a temperature of from 60° to 180° C. for at least 10 minutes, prior to the use of said catalyst slurry in the continuous partial hydrogenation of said aromatic hydrocarbon.

2. The method according to claim 1, wherein said heat treatment is conducted in the presence of a hydrogen gas dissolved in said catalyst slurry.

3. A method for the continuous partial hydrogenation of a monocyclic aromatic hydrocarbon, which comprises:

(1) continuously feeding a monocyclic aromatic hydrocarbon and a hydrogen gas to a reaction zone, and contacting said hydrocarbon and hydrogen with a catalyst slurry comprised mainly of a ruthenium catalyst, a zinc salt and water and performing a partial hydrogenation reaction of said monocyclic aromatic hydrocarbon, said catalyst slurry having been heat-treated substantially in the absence of said monocyclic aromatic hydrocarbon at a temperature of from 60° to 180° C. for at least 10 minutes, while agitating, prior to the use of said catalyst slurry in the continuous partial hydrogenation of said monocyclic aromatic hydrocarbon, thereby obtaining a reaction mixture comprising an oil phase comprised mainly of a partial hydrogenation reaction product and the unreacted aromatic hydrocarbon and an aqueous phase comprised of the catalyst slurry; and (2) continuously introducing said reaction mixture to an oil phase-aqueous phase separation zone to separate said oil phase from said aqueous phase, wherein the continuous partial hydrogenation reaction is conducted with continued stable selectivity.

4. The method according to claim 3, wherein said heat treatment of the catalyst slurry has been conducted in the presence of a hydrogen gas dissolved in said catalyst slurry.

5. The method according to claim 1, wherein said ruthenium catalyst further contains a catalyst component selected from the group consisting of copper, iron, zinc, and silver.

6. The method according to claim 1, wherein said ruthenium catalyst is in the form of a metallic ruthenium particulate.

7. The method according to claim 6, wherein said catalyst slurry further comprises a solid additive selected from the group consisting of oxides and hydroxides of titanium, zirconium, hafnium, niobium, tantalum, chromium, iron, cobalt, aluminum, gallium, silicon, or a hydrate thereof.

8. The method according to claim 1, wherein said ruthenium catalyst comprises ruthenium supported on a carrier.

9. The method according to claim 1, wherein said heat-treating is carried out at a temperature of from 100° to 150° C.

10. The method according to claim 3, wherein said ruthenium catalyst further contains a catalyst component selected from the group consisting of copper, iron, zinc, and silver.

11. The method according to claim 3, wherein said ruthenium catalyst is in the form of a metallic ruthenium particulate.

12. The method according to claim 11, wherein said catalyst slurry further comprises a solid additive selected from the group consisting of oxides and hydroxides of titanium, zirconium, hafnium, niobium, tantalum, chromium, iron, cobalt, aluminum, gallium, silicon, or a hydrate thereof.

13. The method according to claim 12, wherein said ruthenium catalyst is contained in an amount of from $1 \times 10^{-4}$ to $5 \times 10^{-2}$ parts by weight per parts by weight of water.

14. The method according to claim 3, wherein said ruthenium catalyst comprises ruthenium supported on a carrier.

15. The method according to claim 14, wherein said ruthenium catalyst is contained in an amount of from $1 \times 10^{-3}$ to 0.1 parts by weight per parts by weight of water.

16. The method according to claim 3, wherein the partial hydrogenation reaction is carried out at a temperature in the range of 100° to 200° C. and under a hydrogen pressure of 10 to 100 kg/cm$^2$G.

17. The method according to claim 16, wherein said monocyclic aromatic hydrocarbon is selected from the group consisting of benzene, toluene, xylenes, and lower alkylbenzenes wherein the alkyl group has 2–4 carbon atoms.

* * * * *